(12) United States Patent
Kauffmann et al.

(10) Patent No.: US 12,311,363 B2
(45) Date of Patent: May 27, 2025

(54) HBA1c ASSAY SLIDE AND METHOD OF MAKING SAME

(71) Applicant: Siemens Healthcare Diagnostics Inc., Tarrytown, NY (US)

(72) Inventors: Aaron Kauffmann, Elkhart, IN (US); Jeffrey Mayfield, South Bend, IN (US); David Ledden, Elkhart, IN (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 837 days.

(21) Appl. No.: 17/593,310

(22) PCT Filed: Mar. 12, 2020

(86) PCT No.: PCT/US2020/022233
§ 371 (c)(1),
(2) Date: Sep. 15, 2021

(87) PCT Pub. No.: WO2020/190603
PCT Pub. Date: Sep. 24, 2020

(65) Prior Publication Data
US 2022/0143604 A1 May 12, 2022

Related U.S. Application Data

(60) Provisional application No. 62/820,462, filed on Mar. 19, 2019.

(51) Int. Cl.
*B01L 3/00* (2006.01)
*B01F 23/00* (2022.01)
(Continued)

(52) U.S. Cl.
CPC ..... *B01L 3/502707* (2013.01); *B01L 3/50273* (2013.01); *B01L 2200/16* (2013.01);
(Continued)

(58) Field of Classification Search
CPC ........... B01L 3/502707; B01L 3/50273; B01L 2200/16; B01L 2300/087;
(Continued)

(56) References Cited

U.S. PATENT DOCUMENTS 6,077,660 A 6/2000 Wong et al.
2004/0191124 A1 9/2004 Noetzel et al.
(Continued)

FOREIGN PATENT DOCUMENTS

CN 106867881 A1 6/2017

OTHER PUBLICATIONS

International Search Report and Written Opinion of International Application No. PCT/US2020/022233 dated Jul. 28, 2020.

*Primary Examiner* — Jennifer Wecker
*Assistant Examiner* — Oyeleye Alexander Alabi

(57) ABSTRACT

Microfluidic devices, method for making and using same are disclosed. The microfluidic device can be made by applying a reagent in liquid form into a sample treatment site within a substrate base. The substrate base has hydrophilic properties bordering a flow channel, and has an application site, the sample treatment site and an analytical site. The flow channel is sized and configured so as to draw a sample applied into the application site to the analytical site through the sample treatment site by capillary action. The reagent is freeze-dried within the sample treatment site.

16 Claims, 3 Drawing Sheets

(51) Int. Cl.
| | | |
|---|---|---|
| B01F 23/41 | (2022.01) | |
| B01F 101/23 | (2022.01) | |
| B23Q 17/24 | (2006.01) | |
| C07K 14/705 | (2006.01) | |
| C12M 1/34 | (2006.01) | |
| C12Q 1/04 | (2006.01) | |
| C12Q 1/18 | (2006.01) | |
| C12Q 1/686 | (2018.01) | |
| G01N 21/3577 | (2014.01) | |
| G01N 21/359 | (2014.01) | |
| G01N 21/39 | (2006.01) | |
| G01N 21/45 | (2006.01) | |
| G01N 21/64 | (2006.01) | |
| G01N 21/77 | (2006.01) | |
| G01N 21/78 | (2006.01) | |
| G01N 27/414 | (2006.01) | |
| G01N 30/12 | (2006.01) | |
| G01N 30/68 | (2006.01) | |
| G01N 30/70 | (2006.01) | |
| G01N 30/72 | (2006.01) | |
| G01N 30/88 | (2006.01) | |
| G01N 33/00 | (2006.01) | |
| G01N 33/18 | (2006.01) | |
| G01N 33/50 | (2006.01) | |
| G01N 33/53 | (2006.01) | |
| G01N 33/543 | (2006.01) | |
| G01N 33/68 | (2006.01) | |
| G01N 33/74 | (2006.01) | |
| G01N 35/00 | (2006.01) | |
| G01N 35/10 | (2006.01) | |
| G06T 7/00 | (2017.01) | |
| G06T 7/90 | (2017.01) | |
| H10K 10/46 | (2023.01) | |
| H10K 85/00 | (2023.01) | |
| H10K 85/20 | (2023.01) | |

(52) U.S. Cl.
CPC . *B01L 2300/087* (2013.01); *B01L 2300/0887* (2013.01); *B01L 2300/161* (2013.01); *B01L 2400/0406* (2013.01)

(58) Field of Classification Search
CPC ....... B01L 2300/0887; B01L 2300/161; B01L 2400/0406; G01N 33/54366
See application file for complete search history.

(56) References Cited

U.S. PATENT DOCUMENTS

| | | |
|---|---|---|
| 2006/0110283 A1 | 5/2006 | Fish |
| 2007/0004033 A1 | 1/2007 | Unger et al. |
| 2008/0293074 A1 | 11/2008 | Tanaka et al. |
| 2009/0088336 A1 | 4/2009 | Burd et al. |
| 2014/0023565 A1 | 1/2014 | Taylor et al. |
| 2015/0336099 A1 | 11/2015 | Seddon et al. |
| 2016/0038938 A1 | 2/2016 | Chen et al. |
| 2019/0072547 A1 | 3/2019 | Ahn et al. |

HBA1c ASSAY SLIDE AND METHOD OF MAKING SAME

This application claims priority to U.S. Provisional Application No. 62/820,462, filed Mar. 19, 2019, the disclosure of which is incorporated herein by reference in its entirety.

STATEMENT REGARDING FEDERALLY SPONSORED RESEARCH AND DEVELOPMENT

Not Applicable.

BACKGROUND

Point-of-care testing refers generally to medical testing at or near the site of patient care, such as in an emergency room. A desired outcome of such tests is often rapid and accurate lab results to determine a next course of action in the patient care. A number of such point of care tests involve analysis of a blood sample from the patient.

Many of these tests use whole blood, plasma or serum.

The DCA Vantage® Analyzer (commercially offered for sale by Siemens Healthcare Diagnostics) is a semi-automated bench top system used for the quantitative detection of analytes present in a patient's liquid test sample, such as, by way of example only, the determination of hemoglobin (including, without limitation, total hemoglobin and/or glycated hemoglobin (hemoglobin $A_{1c}$ and/or $HbA_{1c}$) concentrations) present in a patient's blood sample. The measurement of hemoglobin $A_{1c}$ concentration is recommended for diagnosis and monitoring the long-term care of persons with diabetes. This assay provides a convenient method for the in vitro measurement of percent concentration of hemoglobin $A_{1c}$ in blood.

The DCA Vantage Analyzer uses a spectrophotometer to analyze the intensity of the predetermined wavelengths of light transmitted through a cartridge optical window. Whole blood is added to the reagent cartridge, the cartridge is inserted into the DCA Vantage Analyzer, and meaningful results are available in about six (6) minutes. All measurements and calculations are performed automatically by the DCA Vantage Analyzer, and the screen displays percent $HbA_{1c}$ at the end of the assay.

The following chemical reaction occurs within the DCA Vantage Analyzer cartridge. The red blood cells are lysed with digitonin to release hemoglobin which then starts to denature. While denaturization is occurring, total hemoglobin is oxidized to methemoglobin by potassium ferricyanide. The methemoglobin then complexes with thiocyanate to form thiocyanmethemoglobin, the colored species that is measured. The extent of color development at the wavelength 531 nanometers is directly proportional to the concentration of total hemoglobin in the sample.

$HbA_{1c}$ is non-enzymatically glycated Hb. The amino group of the N-terminal valine residue of the Hb β-chain reacts with open chain form of D-glucose present in blood forming a Schiff's Base which in turn undergoes an Amadori rearrangement. For the measurement of $HbA_{1c}$, an inhibition latex agglutination assay is used. For instance, an agglutinator (synthetic polymer containing multiple copies of the immunoreactive portion of $HbA_{1c}$) causes agglutination of latex coated with $HbA_{1c}$ specific mouse monoclonal antibody. The immunoreactive portion of $HbA_{1c}$ includes the first four β-chain N-terminal amino acid residues with the valine residue having the Amadori rearranged glucose. This agglutination reaction causes increased scattering of light, which is measured as an increase in absorbance at 531 nm. $HbA_{1c}$ in whole blood specimens competes for the limited number of antibody-latex binding sites causing an inhibition of agglutination and a relative decrease in scattering of light. The decreased scattering is measured as a decrease in absorbance at 531 nanometers. The $HbA_{1c}$ concentration is then quantified using a calibration curve of absorbance versus $HbA_{1c}$ concentration. The percent $HbA_{1c}$ in the sample is then calculated as follows:

$$\% \ HbA_{1c} = ([HbA_{1c}]/[\text{Total Hemoglobin}]) \times 100$$

Both the concentration of hemoglobin $A_{1c}$ and the concentration of total hemoglobin are measured, and the ratio reported as percent hemoglobin $A_{1c}$.

It would be advantageous to reduce the amount of materials involved in creating a cartridge for the next generation DCA Vantage Analyzer, and also decrease the Time to Results (TTR) of the assay relative to the conventional DCA Vantage Analyzer. It is to such an improved microfluidics device, as well as methods and kits related thereto, that the present disclosure is directed.

BRIEF DESCRIPTION OF THE DRAWINGS

The accompanying drawings, which are incorporated in and constitute a part of this specification, illustrate one or more implementations described herein and, together with the description, explain these implementations. In the drawings.

DETAILED DESCRIPTION

Figure 1:
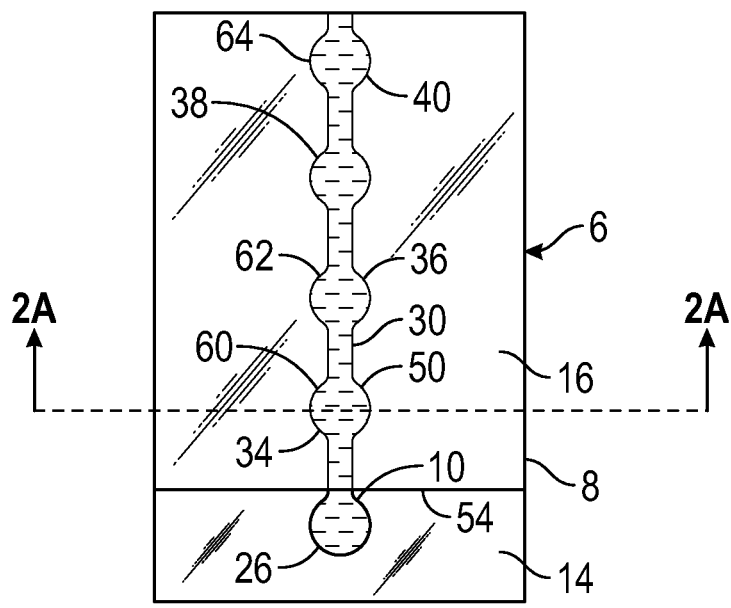
FIG. 1 is a top plan view of an exemplary microfluidic device constructed in accordance with the present disclosure.

The following detailed description refers to the accompanying drawings. The same reference numbers in different drawings may identify the same or similar elements.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements, but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the term "substantially" means that the subsequently described parameter, event, or circumstance completely occurs or that the subsequently described parameter, event, or circumstance occurs to a great extent or degree. For example, the term "substantially" means that the subsequently described parameter, event, or circumstance occurs at least 90% of the time, or at least 91%, or at least 92%, or at least 93%, or at least 94%, or at least 95%, or at least 96%, or at least 97%, or at least 98%, or at least 99%, of the time, or means that the dimension or measurement is within at least 90%, or at least 91% or at least 92%, or at least 93%, or at least 94%, or at least 95%, or at least 96%, or at least 97%, or at least 98%, or at least 99%, of the referenced dimension or measurement.

In accordance with one aspect, there are provided microfluidics devices, formulations, and processes for analyzing a blood sample to determine a concentration of hemoglobin $A_{1c}$, a concentration of total hemoglobin, and to report a ratio of hemoglobin $A_{1c}$ and total hemoglobin as percent hemoglobin $A_{1c}$. In one embodiment, the blood sample can be a whole blood sample that has not been diluted with a diluent.

Material use is reduced by creating a microfluidic device working on the principle of capillary action, and having a configuration in a form of a slide having an internal sample volume in range from about 0.1 µL to about 100 µLs. In one non-limiting embodiment of the presently disclosed and/or inventive concept(s), the internal sample volume is in a range of from about 9.2 µLs to about 11.5 µLs. Creating a microfluidic device based upon capillary action for determining total hemoglobin and hemoglobin $A_{1c}$ thereby yielding the percent $HbA_{1c}$, however, creates additional problems related to having the blood sample properly dissolve at least one reagent within the microfluidic device, including, but not limited to, at least one lysing and oxidation reagent, at least one agglutination reagent, at least one reagent dye, and combinations thereof. The reagent(s) could also include Anti-$A_{1c}$ (anti-human $HbA_{1c}$ antibody), or boronate that are capable of forming reversible covalent complexes with sugars, amino acids, hydroxamic acids, etc. (molecules with vicinal, (1,2) or occasionally (1,3) substituted Lewis base donors (alcohol, amine, carboxylate)).

To accelerate reagent dissolution, the reagent can be freeze dried (i.e., lyophilized) within cavities of predetermined sample treatment sites within the microfluidic device. Freeze drying the reagent within the sample treatment sites may be accomplished by chilling the substrate body, and adding the reagent (in liquid form) into a cavity of a fluid treatment site so that the reagent in liquid form disperses within the cavity to the sidewall(s). The reagent then freezes such that the frozen reagent matches the shape of the cavity. The substrate body having the frozen reagent is placed into a vacuum chamber for a sufficient period of time to dry. In one non-limiting embodiment, the liquid form reagent composition comprises at least one agglutination compound, at least one antibody latex compound, and at least one oxidizing compound.

While the at least one agglutination compound can be any compound(s) capable of accomplishing the presently disclosed inventive concept(s), in one non-limiting embodiment, the at least one agglutination compound comprises or consists of from about 30-60 micrograms/milliliter of at least one agglutination material, at least one protein (such as, by way of example, about 0.1% bovine serum albumin), at least one acid (such as, by way of example, about 20 mM of citric acid), about 75% buffer (as described elsewhere herein), and at least one dye (such as, by way of example, about 0.05 to about 1.0 milligram/milliliter of naphthol green B dye). In one non-limiting embodiment, the at least one agglutination compound of the reagent composition has a pH of about 4.

While the at least one antibody latex compound can be any compound(s) capable of accomplishing the presently disclosed and/or claimed inventive concept(s), in one non-limiting embodiment, the at least one antibody latex compound comprises or consists of about 2.25% to about 3.25% of at least one antibody latex material, at least one protein (such as, by way of example, about 0.75% bovine serum albumin and about 0.25% gelatin), at least one amino acid (such as, by way of example, about 10 mM of glycine), at least one sugar (such as, by way of example, about 5% sucrose and about 5% trehalose), and about 75% buffer (as described elsewhere herein). In one non-limiting embodiment, the at least one antibody latex compound has a pH of about 9.3.

While the at least one oxidizing compound can be any compound(s) capable of accomplishing the presently disclosed and/or claimed inventive concept(s), in one non-limiting embodiment, the at least one non-oxidizing compound comprises or consists of at least one oxidizing material (such as, by way of example, about 15 milligrams/milliliter FeCN), at least one protein (such as, by way of example, about 6% bovine serum albumin), at least one sugar (such as, by way of example, about 5% sucrose), about 75% buffer (as described elsewhere herein), and at least one saponin (such as, by way of example, 0.03% to about 0.3% digitonin).

Freeze drying the liquid form reagent composition within a cavity of the substrate body may require a formulation of the reagent composition having an effective percentage of a buffering solution generally greater than 10%. The effective percentage of the buffering solution may be in a range from about 10% to about 95%. The buffering solution can be phosphate buffered saline, or similar material. The reagent composition may also have an effective percentage of sugar less than about 14% in the reagent.

The sample can be a fluid that has a viscosity permitting the fluid to be drawn by way of capillary action. In certain embodiments, the sample is a whole blood sample which includes red blood cells, white blood cells, and platelets.

Figure 2:
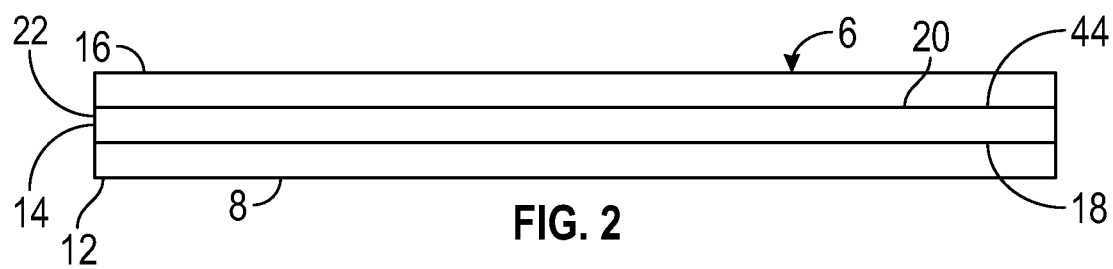
FIG. 2 is a side elevational view of the microfluidic device of FIG. 1.
Figure 2A:
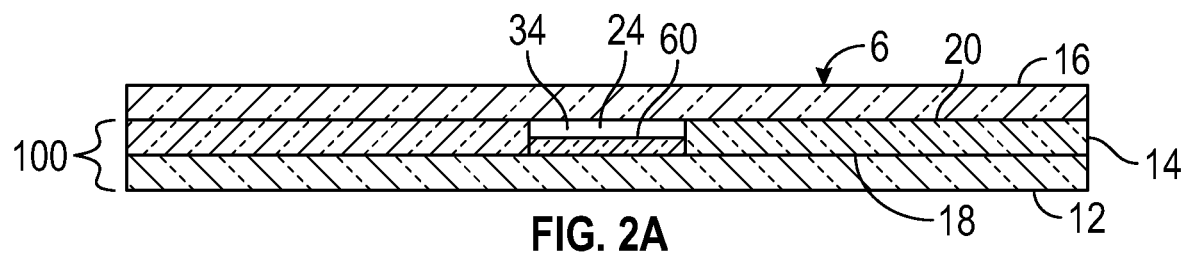
FIG. 2A is a cross-sectional view of the microfluidic device taken along the lines 2A-2A in FIG. 1.

Referring now to FIGS. 1 and 2, shown therein and designated by a reference numeral 6 is a microfluidic device constructed in accordance with the present disclosure. The microfluidic device 6 includes a substrate body 8 having a microfluidic channel structure 10 for the flow transport of a blood sample. In one embodiment, the channel structure 10 has hydrophilic properties, and the motive force moving the blood sample through the microfluidic channel structure 10 is capillary action. The substrate body 8 can be formed of a base layer 12, a core layer 14, and a cover layer 16 (shown in greater detail in FIG. 2).

The core layer 14 overlies the base layer 12, and the cover layer 16 overlies the core layer 14. The core layer 14 has a first major surface 18, a second major surface 20, and an outer peripheral edge 22. To implement the microfluidic channel structure 10, the core layer 14 is provided with a cavity 24 (See FIG. 3) shaped so as to form an application site 26 communicating with a first end 28 of a flow channel 30. The flow channel 30 fluidly connects a first sample treatment site 34, a second sample treatment site 36, a first analytical site 38, and a second analytical site 40. In the example depicted in FIGS. 3 and 4, the flow channel 30 connects the application site 26, the first sample treatment site 34, the second sample treatment site 36, the first analytical site 38, and the second analytical site 40 in a series arrangement, although other arrangements can be used. For the $HbA_{1c}$ assay the flow channel 30 can include an [A1] section including the first sample treatment site 34, and the first analytical site 38, and a [Hb] section including the second sample treatment site 36, and the second analytical site 40 in a parallel arrangement. This can be accomplished by starting with the application site 26 and splitting the flow channel 30 into parallel sections, or using two or more separate application sites 26 to receive the sample. Additional sections of the flow channel 30 can be made for additional/different analytes; such as having a central application site 26 with multiple flow channels radiating outwardly therefrom. In this example, the microfluidic device 26 may be read by indexing the first analytical site 38, and the second analytical site 40 past a reader. Or multiple readers may be used with a first reader reading the first analytical site 38, and a second reader reading the second analytical site 40, for example.

The flow channel 30 also intersects the output peripheral edge 22 so as to form a vent for the flow channel 30. In another embodiment, the cover layer 16 may include an opening (not shown) which is in fluid communication with the flow channel 30 to thereby serve as a vent. In this embodiment, the cavity 24 extends all of the way through the core layer 14, i.e., from the first major surface 18 to the second major surface 20. A first major surface 44 of the cover layer 16 is in substantially direct contact with the second major surface 20 of the core layer 14, and a first major surface 46 of the base layer 12 is in substantially direct contact with the first major surface 18 of the core layer 14. Thus, the core layer 14 forms a sidewall 50 of the flow channel 30, the base layer 12 forms a bottom of the flow channel 30, and the cover layer 16 forms a top of a portion of the flow channel 30. In one non-limiting embodiment, the cover layer 16 does not overlay or overlap with the application site 26 so that the sample of blood can be introduced into the application site 26. As shown in FIG. 1, in one non-limiting embodiment of the presently disclosed and/or claimed inventive concept(s), the application site 26 can be outside of an outer boundary 54 of the cover layer 16. In another non-limiting embodiment, the application site 26 can be within the outer boundary 54 and aligned with an opening of the cover layer 16. The first sample treatment site 34, the second sample treatment site 36 and/or the second analytical site 40 may be generally open, i.e., devoid of obstructions, or include obstructions that permit the sample to flow through the first sample treatment site 34, the second sample treatment site 36 and/or the second analytical site 40 generally from one end to the other end. When obstructions are included in the first sample treatment site 34, the second sample treatment site 36 and/or the second analytical site 40, the obstructions may be configured so as to facilitate mixing between the sample and the first reagent 60, the second reagent 62 and/or the third reagent 64 as the sample passes from the application site 26 towards the vent. When the first sample treatment site 34, the second sample treatment site 36 and/or the second analytical site 40 are generally devoid of obstructions, mixing of the sample with the first reagent 60, the second reagent 62 and/or the third reagent 64 may be facilitated with stimulation from a source external to the microfluidic device 6. For example, an acoustic source (external to the microfluidic device 6) may be used to direct sound waves to the first sample treatment site 34, the second sample treatment site 36 and/or the second analytical site 40 to cause the sample to mix with the first reagent 60, the second reagent 62, and/or the third reagent 64. The source can be a part of a blood analyzer that enables the source to mix the sample with the reagents within the microfluidic device 6, and then reads the results of the assay, e.g., within the first and second analytical sites 38 and 40.

A first reagent 60 is positioned within the first sample treatment site 34, a second reagent 62 is positioned within the second sample treatment site 36, and a third reagent is positioned within the second analytical site 40. In one embodiment, the first, second, and third reagents 60, 62 and 64 are selected for measuring total hemoglobin and $HbA_{1c}$. In this embodiment, a combination of the first and second reagents 60 and 62 include a lysing reagent, an oxidizing reagent, an agglutination reagent, and a reagent dye. In the example discussed below, the first reagent 60 includes a combination of a lysing reagent and an oxidizing reagent for the measurement of total hemoglobin. And, the second reagent 62 includes a combination of an agglutination reagent, and a reagent dye for the measurement of $HbA_{1c}$. It should be understood, however, that the second reagent 62 may include a combination of a lysing reagent and oxidizing reagent, and the first reagent 60 can be a combination of an agglutination reagent, and a reagent dye. The third reagent can be an antibody latex reagent.

For the measurement of total hemoglobin, saponins, including without limitation, digitonin, or other cell lysis reagents can be used to lyse the sample. Potassium ferricyanide can be used to oxidize hemoglobin in the sample to methemoglobin. The methemoglobin then complexes with thiocyanate to form thiocyanmethemoglobin, the colored species that is measured for the determination of total hemoglobin concentration. The extent of color development at the wavelength of about 531 nanometers is directly proportional to the concentration of total hemoglobin in the sample. In other embodiments, the lysing and oxidizing reagent may include other oxidizing agents such as sodium nitrite with sodium azide. A cyanide derivative may also be involved. That is, after methemoglobin forms ($Fe^{+3}$) a cyanide derivative like thiocyanate becomes the sixth position ligand of the heme moiety.

For the measurement of $HbA_{1c}$, an inhibition of latex agglutination assay is used. At least one agglutinator (such as a synthetic polymer containing multiple copies of the immunoreactive portion of $HbA_{1c}$) causes agglutination of latex coated with $HbA_{1c}$ specific mouse monoclonal antibody. This agglutination reaction causes increased scattering of light, which is measured as an increase in absorbance at 531 nanometers. $HbA_{1c}$ in whole blood specimens competes for the limited number of antibody-latex binding sites causing an inhibition of agglutination and a decreased scattering of light. The decreased scattering is measured as a decrease in absorbance at 531 nm. The $HbA_{1c}$ concentration is then quantified using a calibration curve of absorbance versus $HbA_{1c}$ concentration. The percent $HbA_{1c}$ in the sample is then calculated as follows in accordance with formula [1]:

$$\% \ HbA_{1c} = ([HbA_{1c}]/[\text{Total Hemoglobin}]) \times 100 \quad\quad [1]$$

In operation, a sample is deposited in the application site 26, and is passed (e.g., pulled) via capillary action through the flow channel 30 and into the first sample treatment site 34, the second sample treatment site 36, the first analytical site 38, and the second analytical site 40. As the sample passes through the first sample treatment site 34, and the second sample treatment site 36, the sample mixes with the first reagent 60 and the second reagent 62. As discussed herein, the mixing can be assisted with obstructions within the first sample treatment site 34, and the second sample treatment site 36, or by the application of an external medium, e.g., acoustic waves. This causes the sample to by lysed, oxidized and mixed with the agglutinator. The lysed sample passes to the first analytical site 38 where the total hemoglobin is read. The antibody latex reagent positioned in the second analytical site 40 permits determination of the $HbA_{1c}$ of the lysed solution. Variability in agglutinator and the oxidizer concentrations may be corrected for by a dye ratio. In one non-limiting embodiment, the agglutinator reagent, the antibody latex), and FeCN (lysing and oxidation reagents) can be formulated, comprised, or consisted of as follows:

| Agglutinator |
| --- |
| 30-60 ug/mL Agg. |
| 0.1% BSA |
| 20 mM Citric Acid |
| pH 4 |
| 75% Buffer |
| Naphthol Green B 0.05-1 mg/mL Dye |

| Antibody Latex |
| --- |
| 2.25-3.25% AbLx |
| 0.75% BSA |
| 0.25% Gelatin |
| 10 mM Glycine |
| 5% Sucrose |
| 5% Trehalose |
| pH 9.3 |
| 76% Buffer |

| FeCN |
| --- |
| 15 mg/mL FeCN |
| 6% BSA |
| 5% Sucrose |
| 75% Buffer |
| 0.03-0.3% Digitonin |

The base layer 12, the core layer 14, and the cover layer 16 can be constructed of a hydrophilic plastic or a hydrophilic glass. Exemplary plastics include, but are not limited to, acrylic, polycarbonate, cyclic olefin polymer, polystyrene, polyethylene, styrene-acrylonitrile, and polyethylene terephthalate. The plastics or glass may be inherently hydrophilic, or include a hydrophilic surface treatment. Exemplary hydrophilic surface treatments for plastic include, but are not limited to, treatment with ionizing radiation (x-rays, electron beams) in the presence of oxygen, followed by heat-treatment of the peroxidized plastic in presence of an appropriate vinyl monomer. Another method is to introduce peroxy groups onto a plastic surface by ozone treatment. Treatment with plasma (ionized gas) alone can also oxidize and otherwise chemically modify a plastic surface to hydrophilize polyolefins, for example. With respect to glass, surface treatments such as soda lime or borosilicate can be used to create a hydrophilic surface. The base layer 12, the core layer 14, and the cover layer 16 may be transparent to visible light. In one embodiment, the base layer 12 and the core layer 14 may be constructed of material(s) that may be opaque to visible light. With respect to the cover layer 16, visual access to the first analytical site 38 and the second analytical site 40 should be provided so that a spectrophotometer can be used to read the results of the assays, as discussed above. The cover layer 16 can be entirely transparent to visible light, or can be opaque to visible light so long as one or more regions of the cover layer 16 that are transparent to visible light are aligned with the first analytical site 38 and the second analytical site 40. For example, one or more transparent region(s) of the cover layer 16 can overlap with the first analytical site 38 and the second analytical site 40, or overlie the first analytical site 38 and the second analytical site 40. The base layer 12 and the cover layer 16 can include transparent regions aligned with the first analytical site 38 and the second analytical site 40 so that the results of the assays can be read by a spectrophotometer having an excitation source on one side of the substrate body 8, and a photodetector on an opposite side of the substrate body 8. In another embodiment, one of the base layer 12 and the cover layer 16 can include a transparent region aligned with the first analytical site 38 and the second analytical site 40 so that the results of the assays can be read by a spectrophotometer having both the excitation source and the photodetector on a same side of the substrate body 8. The base layer 12, the core layer 14, and the cover layer 16 are connected together so as to form the substrate body 8. Any suitable technique can be used to connect the base layer 12, the core layer 14 and the cover layer 16 together including but not limited to sonic welding, a bonding material such as an adhesive or a cohesive, thermal lamination, and combinations thereof. Although the base layer 12, the core layer 14 and the cover layer 16 are shown by way of example as rectangular, it should be understood that the base layer 12, the core layer 14 and the cover layer 16 can be collectively configured to be any shape(s) capable of accomplishing the presently disclosed and/or claimed inventive concept(s).

Figure 3:
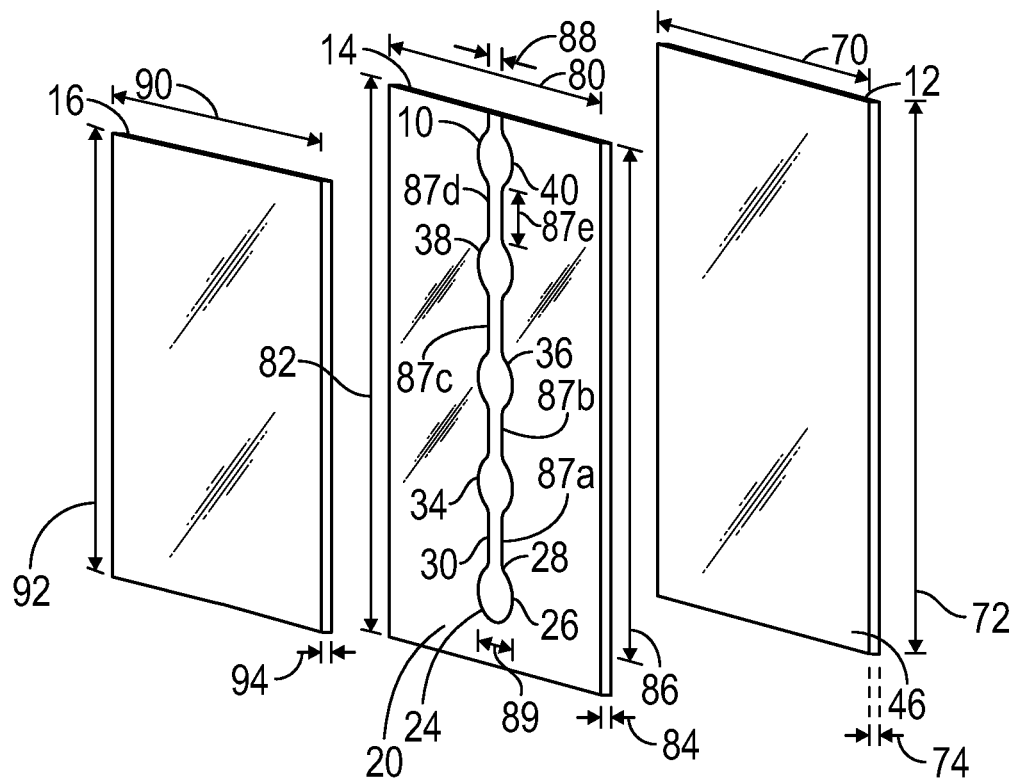
FIG. 3 is an exploded perspective view of the microfluidic device of FIGS. 1 and 2.

As shown in FIG. 3, the base layer 12 has a width 70, a length 72, and a thickness 74. The width 70 can be in a range from about 20 mm to about 40 mm. The length 72 can be in a range from about 30.4 mm to about 70.8 mm. The thickness 74 can be in a range from about 0.1 mm to about 1 mm.

The core layer 14 is also provided with a width 80, a length 82, and a thickness 84. The width 80 can be in a range from about 20 mm to about 40 mm. The length 82 can be in a range from about 30.4 mm to about 70.8 mm. The thickness 84 can be in a range from about 0.065 mm to about 0.195 mm.

The microfluidic channel structure 10 includes a length 86, a first width 88, and a second width 89. The length 86 of the microfluidic channel structure 10 is less than the length 82 of the core layer 14. The first width 88, of microfluidic segments 87a, 87b, 87c, 87d fluidly connecting the application site 26, the first sample treatment site 34, the second sample treatment site 36, the first analytical site 38 and the second analytical site 40, can be in a range from about 0.1 mm to about 20 mm. The microfluidic segments 87a, 87b, 87c, and 87d may have a length 87e in a range from about 0.0 to 20 mm. When the length of the microfluidic segments 87a, 87b, 87c, or 87d are 0, the adjacent analytical/treatment areas will be touching so as to provide a fluid connection having the width 88. The second width 89, of the application site 26, the first sample treatment site 34, the second sample treatment site 36, the first analytical site 38, and the second analytical site 40, can be in a range from about 0.5 mm to about 20 mm. For example, the length 86 can be within a range from about 25.4 mm to about 50.8 mm. The second width 89 may be larger than the first width 88.

The cover layer 16 includes a width 90, a length 92, and a thickness 94. The width 90 of the cover layer 16 can be in a range from about 20 mm to about 40 mm. The length 92 of the cover layer 16 can be in a range from about 5.4 mm to about 45.5 mm. The thickness 94 of the cover layer 16 can be in a range from about 0.1 mm to about 1 mm. The length 92 of the cover layer 16 may be less than the length 82 of the core layer 14 so that the application site 26 is open and capable of receiving the sample. In another embodiment, the length 92 of the cover layer 16 may be the same as the length 82 of the core layer 14. In this embodiment, the cover layer 16 may have an opening aligned with the application site 26 to as to permit the sample to be applied to the application site 26.

The microfluidic device 6 may be formed in a variety of ways. For example, a substrate base 100 (See FIG. 4) of the substrate body 8 may be formed by connecting the base layer 12 to the core layer 14 (having the cavity 24 shown in FIG. 3). The substrate base 100 includes the flow channel 30 having the application site 26, the first sample treatment site 34, the second sample treatment site 36, the first analytical site 38, and the second analytical site 40 in fluid communication via the flow channel 30. In other embodiments, the portion of the substrate body 8 (shown in FIG. 1) may be formed by etching or otherwise forming the cavity 24 into the substrate base 100. In one embodiment, the first reagent 60, the second reagent 62 and the third reagent 64 may be freeze-dried within the cavity 24 of the substrate body 8. In this embodiment, the substrate base 100 of the substrate body 8 may be chilled to a temperature below freezing, such as about −50° C. to about −70° C. Once the substrate base 100 is chilled, the first reagent 60 may be applied to the first sample treatment site 34, and the second reagent 62 may be applied to the second sample treatment site 36. In one non-limiting embodiment, the first reagent 60 is in a liquid form and is applied to the first sample treatment site 34 such that the first reagent 60 disperses within the first sample treatment site 34 and assumes the shape of the first sample treatment site 34 prior to freezing into a solid state. Likewise, the second reagent 62 and the third reagent 64 may also be applied in a liquid form to the second sample treatment site 36 and the second analytical site 40 such that the second reagent 62 and the third reagent 64 disperse within the respective second sample treatment site 36 or second analytical site 40 and assumes the shape of the second sample treatment site 36 or second analytical site 40 prior to freezing into a solid state. Thereafter, the substrate base 100 having the first reagent 60, the second reagent 62, and third reagent 64 in solid form is placed into a vacuum environment having a temperature less than about 32° C. to remove ice by sublimation to freeze dry the first reagent 60, the second reagent 62, and the third reagent within the first sample treatment site 34, the second sample treatment site 36, and the second analytical site 40. The term "ice", as used herein, refers to a crystalline solid, such as frozen water. Once the first reagent 60, the second reagent 62, and the third reagent 64 are freeze dried, the portion of the substrate body 8 can be removed from the vacuum environment, and the cover layer 16 applied and connected thereto to cover the first sample treatment site 34, the second sample treatment site 36, the first analytical site 38, and the second analytical site 40 and form the substrate body 8 having the microfluidic channel structure 10. In other embodiments, the first reagent 60, the second reagent 62, and/or the third reagent 64 can be placed within the cavity 24 of the substrate base 100 in solid form as lyophilized particulates.

Figure 4:
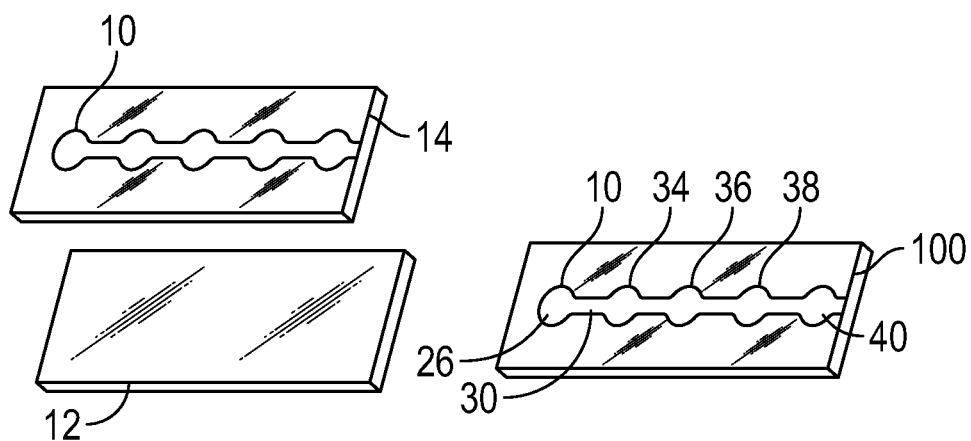
FIGS. 4-7 illustrate exemplary steps in forming the microfluidic device in accordance with the present disclosure.
Figure 5:
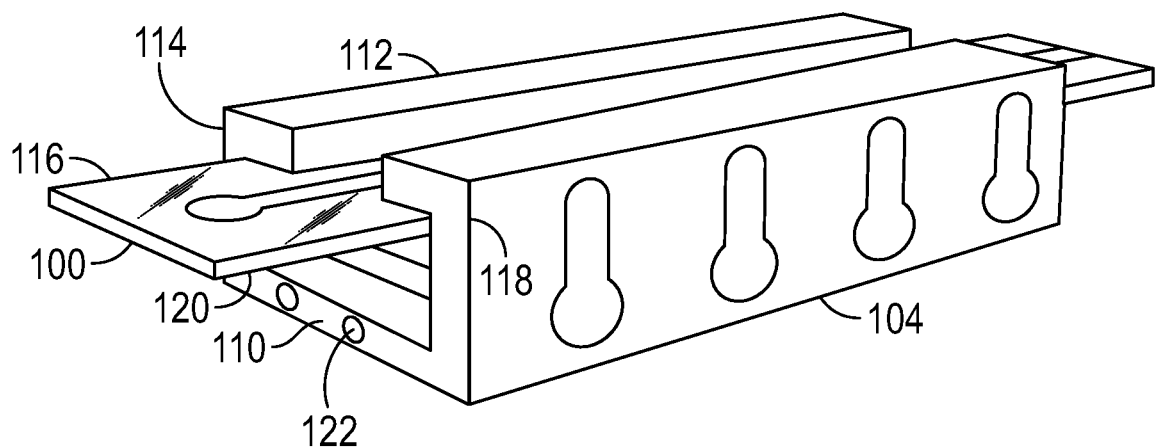
Figure 6:
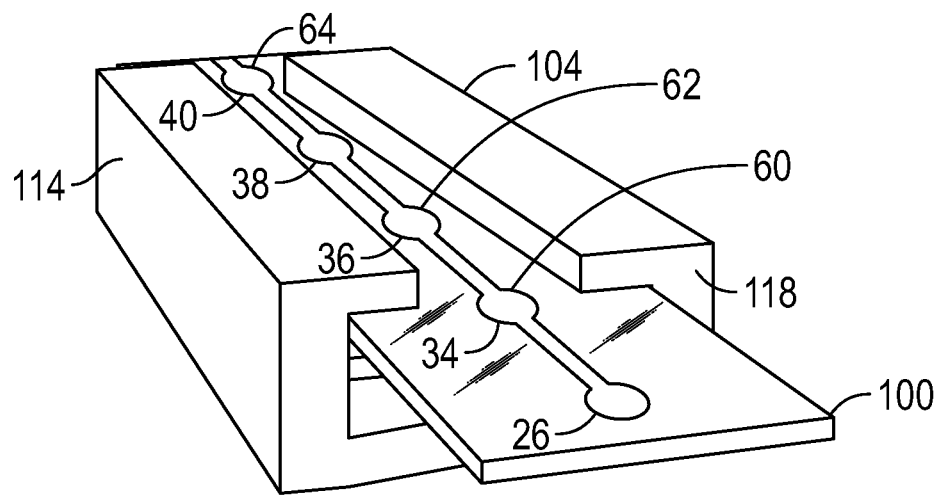
Figure 7:
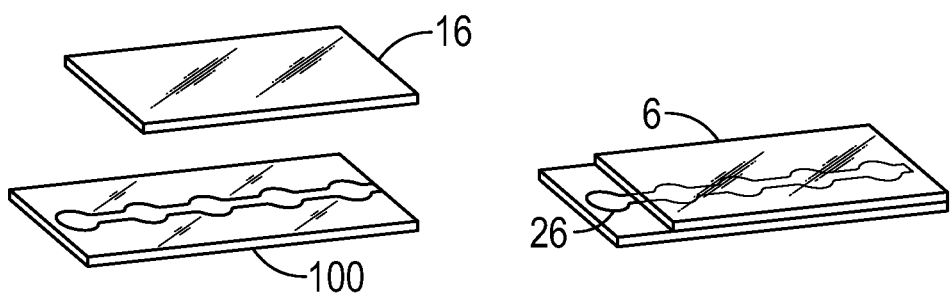

FIGS. 4-7 illustrate exemplary steps in forming the microfluidic device 6 in accordance with the present disclosure. FIG. 4 shows the core layer 14 being connected to the base layer 12 to form the substrate base 100. Once the substrate base 100 is formed, the substrate base 100 can then be inserted to a chiller 104 to cool the substrate base 100 to a temperature below freezing that may be within a range from about −50° C. to about −70° C. The chiller 104 may be in various forms so long as the chiller 104 can cool the substrate base 100 as described above. In the example shown, however, the chiller 104 includes a base 110 made of a thermally conductive material having a chilled track 112. The base 110 that may be constructed of one or more thermally conductive material such as a metal, or a combination of metal enclosing a gas to remove heat from the substrate base 100. In the embodiment shown, the chilled track 112 includes a first track 114 for receiving a first edge 116 of the substrate base 100, and a second track 118 for receiving a second edge 120 of the substrate base 100. The base 110 may be provided with one or more bores 122 for receiving a chilled fluid. The chilled fluid may be in a temperature range from about −50° C. to about −70° C. Once the substrate base 100 has been chilled to within the range of about −50° C. to about −70° C., the first reagent 60, the second reagent 62, and the third reagent 64 are applied as shown in FIG. 6. The substrate base 100 having the first reagent 60, the second reagent 62, and the third reagent 64 is then placed into a vacuum chamber for a suitable period of time until the first reagent 60, the second reagent 62, and the third reagent 64 are freeze dried. The period of time can vary depending upon a variety of factors, such as the temperature within the vacuum chamber, and then, as shown in FIG. 7, the cover layer 16 is applied and connected to the substrate base 100.

Non-Limiting Examples of the Inventive Concept(s)

A microfluidic device, comprising: a substrate body having a microfluidic channel structure for the flow transport of a sample from an application site to at least one analytical site, wherein the microfluidic channel structure comprises a sample treatment site having a sidewall defining a cavity having a shape, the cavity containing a reagent for causing an effect to the sample, the reagent being lyophilized and having a shape matching at least a portion of the shape of the cavity.

The microfluidic device, wherein the reagent is selected from a group consisting of a lysing and oxidizing reagent, an agglutination reagent, and a reagent dye.

The microfluidic device, wherein the substrate body includes hydrophilic properties so as to draw the sample from the application site to the analytical site through the sample treatment site.

The microfluidic device, wherein the substrate body includes a base layer, a core layer, and a cover layer, with the core layer positioned between the base layer and the cover layer, and wherein the microfluidic channel structure is formed within the core layer.

The microfluidic device, wherein the microfluidic channel structure includes a first channel segment between the application site and the at least one sample treatment site, and a second channel segment between the at least one sample treatment site.

The microfluidic device, wherein the sample treatment site has a teardrop shape.

A method for making a microfluidic device, comprising: applying a reagent in liquid form into a sample treatment site within a substrate base, the substrate base having hydrophilic properties bordering a flow channel, and having an application site, a sample treatment site and an analytical site, the flow channel being sized and configured so as to draw a sample applied into the application site to the analytical site through the sample treatment site by capillary action; and freeze-drying the reagent within the sample treatment site.

The method for making the microfluidic device, wherein subsequent to freeze-drying the reagent within the sample treatment site, the method further comprises applying a cover layer on the substrate base so as to encapsulate the sample treatment site and the analytical site, the cover layer having a region that is transparent to visible light and aligned with the analytical site.

The method for making the microfluidic device, wherein freeze-drying the reagent within the sample treatment site includes chilling the substrate base prior to the application of the reagent in liquid form into the cavity.

The method for making the microfluidic device, wherein chilling the substrate base is defined further as chilling the substrate base to a temperature within a range from about −50° C. to about −70° C.

The method for making the microfluidic device, wherein the reagent is a first reagent and the sample treatment site is a first sample treatment site, wherein the flow channel includes a second sample treatment site, and further comprising applying a second reagent in liquid form into the second sample treatment site, and freeze-drying the second reagent in the second sample treatment site.

The method for making the microfluidic device, wherein the sample is blood, the first reagent is a lysing and oxidizing reagent, and the second reagent is an agglutinator reagent.

The method for making the microfluidic device, wherein subsequent to freeze-drying the reagent within the sample treatment site, the method further comprises applying a cover layer on the substrate base so as to encapsulate the first sample treatment site, the second sample treatment site, and the analytical site, the cover layer having a region that is transparent to visible light and aligned with the analytical site.

The method for making the microfluidic device, wherein the analytical site is a first analytical site, and the region is a first region, and wherein the flow channel further comprises a second analytical site, and wherein the cover layer has a second region transparent to visible light and aligned with the second analytical site.

A method, comprising: applying a sample to an application site of a substrate body having a microfluidic channel structure for the flow transport of the sample from the application site to at least one analytical site, wherein the microfluidic channel structure comprises a sample treatment site having a sidewall defining a cavity having a shape, the cavity containing a reagent for causing an effect to the sample, the reagent being lyophilized and having a shape matching the shape of the cavity, wherein the sample mixes with the reagent as the sample passes from the application site, through the sample treatment site to the analytical site to form a sample reagent mixture; and placing the substrate body into a reader so as to determine an effect of the reagent on the sample.

A composition, comprising: a liquid form reagent selected from the group consisting of: at least one liquid agglutination compound having a first volume, wherein the at least agglutination compound comprises at least one agglutination material, at least one protein, at least one acid, at least one buffer comprising at least 15% of the first volume, and at least one dye; at least one liquid antibody latex compound having a second volume, wherein the at least one antibody latex compound comprises at least one antibody latex material, at least one protein, at least one amino acid, at least one sugar, and at least one buffer comprising at least 15% of the second volume; and at least one liquid oxidizing compound having a third volume, wherein the at least one oxidizing compound comprises at least one oxidizing material, at least one protein, at least one sugar, at least one buffer comprising at least 15% of the third volume, and at least one saponin.

The composition, wherein the at least one dye is naphthol green B.

The composition, wherein at least one buffer is a phosphate buffered saline solution.

The composition, wherein the at least one protein is selected from the group consisting of bovine serum albumin, gelatin, and combinations thereof.

The composition, wherein the at least one sugar is selected from the group consisting of sucrose, trehalose, and combinations thereof.

From the above description, it is clear that the inventive concepts disclosed herein are well adapted to carry out the objects and to attain the advantages mentioned herein as well as those inherent in the inventive concepts disclosed herein. While presently preferred embodiments of the inventive concepts disclosed herein have been described for purposes of this disclosure, it will be understood that numerous changes may be made which will readily suggest themselves to those skilled in the art and which are accomplished within the scope and coverage of the inventive concepts disclosed and claimed herein.

What is claimed is:

1. A microfluidic device, comprising: a substrate body having a microfluidic channel structure for the flow transport of a sample from an application site to at least one analytical site, wherein the microfluidic channel structure comprises a sample treatment site having a sidewall defining a cavity having a shape, the cavity containing a reagent configured to cause an effect to the sample, such that the reagent is configured to be lyophilized within the cavity.

2. The microfluidic device of claim 1, wherein the reagent is selected from a group consisting of a lysing and oxidizing reagent, and a reagent dye.

3. The microfluidic device of claim 2, wherein the group also includes an agglutination reagent.

4. The microfluidic device of claim 1, wherein the substrate body includes hydrophilic properties so as to draw the sample from the application site to the analytical site through the sample treatment site.

5. The microfluidic device of claim 1, wherein the substrate body includes a base layer, a core layer, and a cover layer, with the core layer positioned between the base layer and the cover layer, and wherein the microfluidic channel structure is formed within the core layer.

6. The microfluidic device of claim 1, wherein the microfluidic channel structure includes a first channel segment between the application site and the at least one sample treatment site, and a second channel segment between the at least one sample treatment site and the at least one analytical site.

7. The microfluidic device of claim 1, wherein the sample treatment site has a teardrop shape.

8. A method for making a microfluidic device, comprising:
applying a reagent in liquid form into a sample treatment site within a substrate base, the substrate base having hydrophilic properties bordering a flow channel, and having an application site, a sample treatment site and an analytical site, the flow channel being sized and configured so as to draw a sample applied into the application site to the analytical site through the sample treatment site by capillary action; and
lyophilizing the reagent within the sample treatment site.

9. The method for making the microfluidic device of claim 8, wherein subsequent to lyophilizing the reagent within the sample treatment site, the method further comprises applying a cover layer on the substrate base so as to encapsulate the sample treatment site and the analytical site, the cover layer having a region that is transparent to visible light and aligned with the analytical site.

10. The method for making the microfluidic device of claim 8, wherein lyophilizing the reagent within the sample treatment site includes chilling the substrate base prior to the application of the reagent in liquid form into the cavity.

11. The method for making the microfluidic device of claim 10, wherein chilling the substrate base is defined further as chilling the substrate base to a temperature within a range from about −50° C. to about −70° C.

12. The method for making the microfluidic device of claim 8, wherein the reagent is a first reagent and the sample treatment site is a first sample treatment site, wherein the flow channel includes a second sample treatment site, and further comprising applying a second reagent in liquid form into the second sample treatment site, and lyophilizing the second reagent in the second sample treatment site.

13. The method for making the microfluidic device of claim 12, wherein the sample is blood, the first reagent is a lysing and oxidizing reagent, and the second reagent is an agglutinator reagent.

14. The method for making the microfluidic device of claim 13, wherein subsequent to lyophilizing the reagent within the sample treatment site, the method further comprises applying a cover layer on the substrate base so as to encapsulate the first sample treatment site, the second sample treatment site, and the analytical site, the cover layer having a region that is transparent to visible light and aligned with the analytical site.

15. The method for making the microfluidic device of claim 14, wherein the analytical site is a first analytical site, and the region is a first region, and wherein the flow channel further comprises a second analytical site, and wherein the cover layer has a second region transparent to visible light and aligned with the second analytical site.

16. A method, comprising:
applying a sample to an application site of a substrate body having a microfluidic channel structure for the flow transport of the sample from the application site to at least one analytical site, wherein the microfluidic channel structure comprises a sample treatment site having a sidewall defining a cavity having a shape, the cavity containing a reagent configured to cause an effect to the sample, such that the reagent is configured to be lyophilized within the cavity, wherein the sample mixes with the reagent as the sample passes from the application site, through the sample treatment site to the analytical site to form a sample reagent mixture; and
placing the substrate body into a reader so as to determine the effect of the reagent on the sample.

\* \* \* \* \*